(12) United States Patent
Dressler et al.

(10) Patent No.: US 8,470,599 B2
(45) Date of Patent: Jun. 25, 2013

(54) RENAL PROGENITOR CELLS FROM EMBRYONIC STEM CELLS

(75) Inventors: Gregory R. Dressler, Ann Arbor, MI (US); Doyeob Kim, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 133 days.

(21) Appl. No.: 12/837,169

(22) Filed: Jul. 15, 2010

(65) Prior Publication Data

US 2010/0297757 A1 Nov. 25, 2010

Related U.S. Application Data

(63) Continuation of application No. 11/488,291, filed on Jul. 18, 2006, now abandoned.

(60) Provisional application No. 60/700,234, filed on Jul. 18, 2005.

(51) Int. Cl.
*C12N 5/00* (2006.01)

(52) U.S. Cl.
USPC ........................ 435/377; 435/325; 435/375

(58) Field of Classification Search
None
See application file for complete search history.

(56) References Cited

U.S. PATENT DOCUMENTS

| | | | | |
|---|---|---|---|---|
| 5,837,507 | A * | 11/1998 | Largman et al. | 424/93.21 |
| 2002/0006663 | A1 * | 1/2002 | Scadden et al. | 435/455 |
| 2003/0049799 | A1 * | 3/2003 | Schwartz et al. | 435/69.7 |
| 2003/0190704 | A1 * | 10/2003 | Xie | 435/69.1 |

OTHER PUBLICATIONS

Yokoo T et al. 2005. Human mesenchymal stem cells in rodent whole-embryo culture are reprogrammed to contribute to kidney tissues. Proc Natl Acad Sci USA 102: 3296-3300.*
McTaggart SJ et al. 2007. Mesenchymal stem cells: Immunobiology and therapeutic potential in kidney disease. Nephrol 12: 44-52.*
Wobus AM et al. 1997. Retinoic Acid Accelerates Embryonic Stem Cell-Derived Cardiac Differentiation and Enhances Development of Ventricular Cardiomyocytes. J Mol Cell Cardiol 29: 1525-1539.*
Luo G et al. 1995. BMP-7 is an inducer of nephrogenesis, and is also required for eye development and skeletal patterning. Genes Dev 8: 2808-2820.*
Dressler G.R. "Development of the Excretory System in Mouse Development: Patterning, Morphogenesis, and Organogenesis" 2002 pp. 395-420.
Bouchard M. et al., "Nephric lineage specification by Pax2 and Pax8." Genes Dev 2002 vol. 16 pp. 2958-2970.
Mauch T.J. et al., "Signals from trunk paraxial mesoderm induce pronephros formation in chick intermediate mesoderm" Dev Biol 2000 vol. 220 62-75.
Herzlinger D. et al., "Metanephric mesenchyme contains multipotent stem cells whose fate is restricted after induction" Development 1992 vol. 114 pp. 565-572.
Yu J. et al., "Recent genetic studies of mouse kidney development." Curr Opin Genet Dev 2004 vol. 14 pp. 550-557.
Humes et al., "Effects of transforming growth factor-beta, transforming growth factor-alpha, and other growth factors on renal proximal tubule cells." Lab. Invest. 1991 vol. 64 pp. 538-545.
Norman et al., "EGF-induced mutagenesis in proximal tubular cells: potentiation by angiotensin II." Am. J. Physiol. 1987 vol. 253 pp. F299-F309.
Dziadek et al., "Expression of nidogen and laminin in basement membranes during mouse embryogenesis and in teratocarcinoma cells." Devel. Biol.1985 vol. 111 pp. 372-382.
Vasios et al., "A retinoic acid-responsive element is present in the 5' flanking region of the laminin B1 gene." Proc. Natl. Acad. Sci. 1989 vol. 86 pp. 9099-9103.
Rogers et al., "Gene expression in visceral endoderm: a comparison of mutant and wild-type F9 embryonal carcinoma cell differentiation." J. Cell Biol. 1990 vol. 110 pp. 1767-1777.
Fissell W.H. and Humes H.D., "Cell therapy of renal failure." Transplant Proc 2003 vol. 35 pp. 2837-2842.
Hollnagel A. et al., "Id genes are direct targets of bone morphogenetic protein induction in embryonic stem cells." J. Biol. Chem. 1999 vol. 274 pp. 19838-19345.
Wiles M.V. et al., "Embryonic stem cell development in a chemically defined medium." Exp. Cell. Res. 1999 vol. 247 pp. 241-248.
Komaki M. et al., "MyoD enhances BMP7-induced osteogenic differentiation of myogenic cell cultures." J. Cell. Sci. 2004 vol. 117(8) pp. 1457-1468.
Slager H.G. et al., "Transforming growth factor-beta in the early mouse embryo: implications for the regulation of muscle formation and implantation." Dev. Genet. 1993 vol. 14 pp. 212-224.
Bain G. et al., "Embryonic stem cells express neuronal properties in vitro." Dev. Biol. 1995 vol. 168 pp. 342-357.
Mongan, NP, et al., (2007), Diverse actions of retinoid receptors in cancer prevention and treatment. Differentiation 75:853-870.
Watabe, T., et al., (2009) Roles of TGF-beta family signaling in stem cell renewal and differentiation. Cell Res 19:103-115.
Valdimarsdottir, G., et al., (2005) Functions of the TGFbeta superfamily in human embryonic stem cells. APMIS 113:773-779.

* cited by examiner

*Primary Examiner* — Lora E Barnhart Driscoll
(74) *Attorney, Agent, or Firm* — Casimir Jones S.C.

(57) ABSTRACT

The present invention relates to compositions and methods for inducing the differentiation of stem cells into renal progenitor cells. In particular, the present invention provides compositions containing activin-a, retinoic acid, and bmp-7, and variants thereof, for differentiating stem cells into renal cells containing tubular epithelia. In certain embodiments, the present invention provides stem cells cultured with compositions used to treat renal disease.

2 Claims, 5 Drawing Sheets

RENAL PROGENITOR CELLS FROM EMBRYONIC STEM CELLS

CROSS REFERENCE TO RELATED APPLICATIONS

This application is a continuation of pending U.S. patent application Ser. No. 11/488,291, filed Jul. 18, 2006, which claims priority to expired U.S. Provisional Patent Application No. 60/700,234, filed Jul. 18, 2005, all of which are herein incorporated by reference in their entireties.

STATEMENT REGARDING FEDERALLY SPONSORED RESEARCH OR DEVELOPMENT

This invention was made with government support under grant number DK069689 awarded by the National Institutes of Health. The government has certain rights in the invention.

FIELD OF THE INVENTION

The present invention relates to compositions and methods for inducing the differentiation of stem cells into renal progenitor cells. In particular, the present invention provides compositions containing activin-a, retinoic acid, and bmp-7, and variants thereof, for differentiating stem cells into renal cells containing tubular epithelia. In certain embodiments, the present invention provides stem cells cultured with compositions used to treat renal disease.

BACKGROUND OF THE INVENTION

Kidney disease is a major health problem in the United States, afflicting some eight million Americans. Kidney and urinary tract diseases together affect an estimated 20 million people, causing more than 95,000 deaths a year and contributing to an additional quarter of a million. Kidney disorders run the gamut from minor infections to total kidney failure. Kidney disease can cause high blood pressure, anemia, and elevated cholesterol. When chronic, it can lead to depression and sexual dysfunction. Kidney stones, diagnosed in more than one million Americans annually, can be extremely painful and are a significant cause of hospital stays and lost work days.

There are many different kinds of kidney diseases. A disease of the kidney may be a short-term problem, and in this case might not cause permanent kidney damage. Examples include some kidney infections and kidney stones. Dehydration, trauma, and some medications can also cause temporary changes in kidney function. "Acute renal failure" is a sudden or rapid loss of kidney function. Acute failure may be reversed, or it may sometimes lead to permanent loss of kidney function.

More often, diseases that affect the kidney are chronic problems. "Chronic renal failure" is a loss of kidney function that occurs gradually and is often "silent," going undetected for months or years. In this case, once it is detected, kidney function may be monitored by periodic blood or urine tests from year to year. Examples of chronic diseases that cause kidney damage over many years are high blood pressure, diabetes, and polycystic kidney disease. When the kidneys permanently lose ninety percent or more of their function, a person is diagnosed with "end-stage renal disease."

Diagnosis and treatment of kidney problems have improved significantly in the past 30 years. Even individuals with complete kidney failure can now lead reasonably normal lives because of modern dialysis techniques and new successes in transplantation. Today dialysis keeps alive more than 120,000 Americans who would otherwise perish because of kidney failure. Kidney transplants, first performed in the United States some 30 years ago, have saved the lives of thousands more.

Treatments for kidney disease such as dialysis and organ transplantation, however, are used as a last resort of treatment and presents serious risks to an individual suffering from a kidney disease. What is needed is an improved understanding of the pathophysiology of kidney disease and improved treatment options for treating kidney disease.

SUMMARY OF THE INVENTION

The present invention relates to compositions and methods for inducing the differentiation of stem cells into renal progenitor cells. In particular, the present invention provides compositions containing activin-a, retinoic acid, and bmp-7, and variants thereof, for differentiating stem cells into renal cells containing tubular epithelia. In certain embodiments, the present invention provides stem cells cultured with compositions used to treat renal disease.

In certain embodiments, the present invention provides a method for differentiating stem cells into renal epithelial cells comprising a) providing stem cells and a composition comprising a first agent capable of activating the retinoic acid signaling pathway, a second agent capable of activating the activin-a pathway, and a third agent capable of activating the bmp-7 pathway; and b) culturing the stem cells with the composition.

In preferred embodiments, the culturing generates a population of renal epithelial cells. In preferred embodiments, the stem cells are embryonic stem cells.

In some embodiments, the present invention provides a population of cells generated by such methods.

In preferred embodiments, the method further comprises providing a host and transplanting at least a portion of the population of stem cells into the host. In preferred embodiments, the stem cells are provided from the host.

In preferred embodiments, the culturing is under conditions whereby the cells retain their pluripotential phenotype after expansion. In preferred embodiments, the stem cells comprise human stem cells.

In certain embodiments, the present invention provides a composition comprising a) stem cells; and b) retinoic acid, activin-a, and bmp-7 in sufficient concentration to induce differentiation of the stem cells into renal epithelial cells. In preferred embodiments, the stem cells are embryonic stem cells.

In certain embodiments, the present invention provides a kit comprising a) a differentiation cocktail consisting of retinoic acid, activin-a, and bmp-7; and b) accessory reagents.

In certain embodiments, the present invention provides a method of generating renal proximal tubule cells, comprising a) providing stem cells cultured with a composition comprising a first agent capable of activating the retinoic acid signaling pathway, a second agent capable of activating the activin-a pathway, and a third agent capable of activating the bmp-7 pathway, and cultured kidney rudiments; b) contacting the stem cells cultured with the composition with the cultured kidney rudiments; and c) culturing the cultured kidney rudiments under conditions such that the rudiments develop proximal tubule cells. In preferred embodiments, the stem cells are embryonic stem cells.

DEFINITIONS

Figure 1:
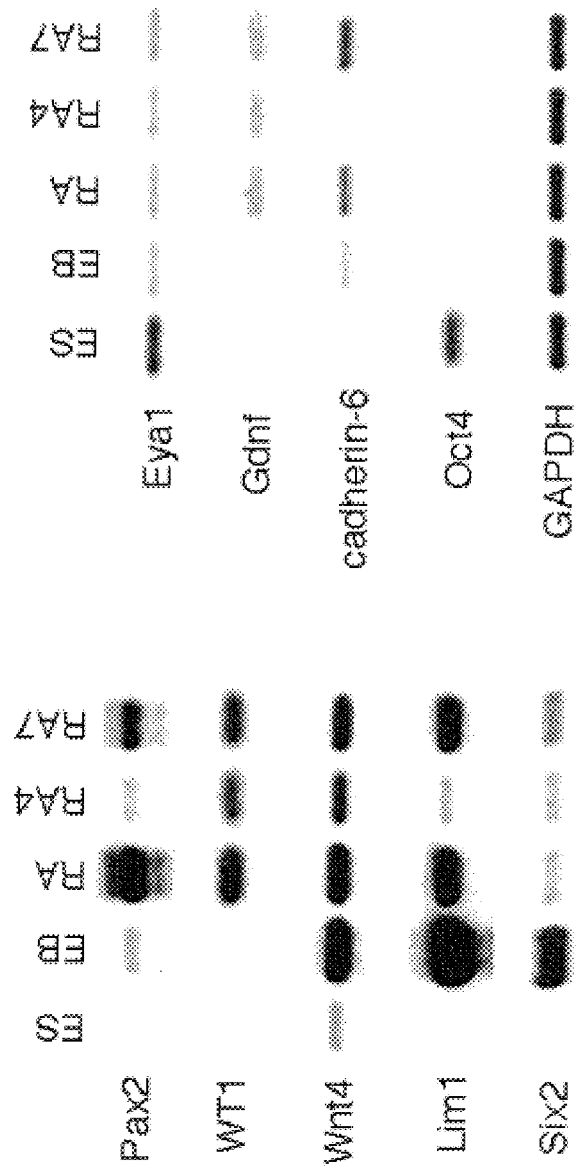
FIG. 1 shows gene expression analysis in EBs after addition of differentiation promoting factors. Total RNA was extracted from cells after 5 days culture with control media or addition of growth factors and assayed for gene specific expression by semi-quantitative RT-PCR. Lanes are as follows: ES, undifferentiated ES cells; EB, embryoid bodies without growth factors or LIF; RA, EBs with 0.1 µM retinoic acid and 10 ng/ml Avtivin-A; RA4, 0.1 µM retinoic acid, 10 ng/ml activin-a and 50 ng/ml BMP4; RA7, 0.1 µM retinoic acid, 10 ng/ml activin-a and 50 ng/ml BMP-7. Input RNAs were adjusted so that equal amounts of GAPDH were amplified in each sample.

To facilitate an understanding of the present invention, a number of terms and phrases are defined below:

A "differentiation agent," as used herein, refers to one of a collection of compounds that are used in culture systems to produce differentiated cells of a renal lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others, or acting in concert with other agents through unknown mechanisms. Examples of differentiation agents include, but are not limited to, activin-a, bmp-7, and retinoic acid.

The term, "cocktail," as used in this disclosure, refers to a composition containing two or more agents useful in differentiating stem cells (e.g., two or more of activin-a, bmp-7, and retinoic acid).

The term "retinoic acid signaling pathway," as used in this disclosure, refers to any molecular pathway involving retinoic acid (e.g., any pathway which is influenced by retinoic acid). Such a pathway may be activated by retinoic acid or by homologues or mimics of retinoic acid function (e.g., retinoic acid receptor agonists).

The term "activin-a signaling pathway," as used in this disclosure, refers to any molecular pathway involving activin-a (e.g., any pathway which is influenced by activin-a). Such a pathway may be activated by activin-a or by homologues or mimics of activin-a function (e.g., activin-a receptor agonists).

The term "bmp-7 signaling pathway," as used in this disclosure, refers to any molecular pathway involving bmp-7 (e.g., any pathway which is influenced by bmp-7). Such a pathway may be activated by bmp-7 or by homologues or mimics of bmp-7 function (e.g., bmp-7 receptor agonists).

The term "embryoid bodies" is a term of art synonymous with "aggregate bodies." The terms refer to aggregates of differentiated and undifferentiated cells that appear when embryonic stem cells overgrow in monolayer cultures, or are maintained in suspension cultures. Embryoid bodies are a mixture of different cell types, typically from several germ layers, distinguishable by morphological criteria and cell markers detectable by immunocytochemistry.

As used herein, the "expansion" of a stem cell indicates that there is an increase in the absolute number of stem cells (e.g., during the culturing of the cells). Analogously, a stem cell that has undergone such expansion has been "expanded."

As used herein, the term "transplant" refers to tissue used in grafting, implanting, or transplanting, as well as the transfer of tissues from one part of the body to another, the return of cells to the original donor (autologous transplants) or the transfer of tissues from one individual to another, or the introduction of biocompatible materials into or onto the body. The term "transplantation" refers to the grafting of or placement of tissues from one part of the body to another part, or to another individual.

The term "renal disease," "renal disorder," "kidney disease," or "kidney disorder," refers to any disease or disorder afflicting the kidney system. Examples of renal diseases include, but are not limited to, nephritis, nephropathy, hyperfiltration, mild microalbuminuria, clinical albuminuria, kidney failure, polycystic kidney disease, and chronic renal insufficiency.

The term "subject suffering from a renal disease" as used herein, refers to both humans and animals displaying symptoms normally associated with a disease that affects the renal system. The term "animals" refers to all non-human animals. Such non-human animals include, but are not limited to, vertebrates such as rodents, non-human primates, ovines, bovines, lagomorphs, porcines, caprines, equines, canines, felines, ayes, etc.

As used herein, the term "sample" refers broadly to all types of samples obtained from humans and other animals, including but not limited to, body fluids such as urine, blood, fecal matter, cerebrospinal fluid (CSF), semen, and saliva, as well as solid tissue. These examples are not to be construed as limiting the sample types applicable to the present invention.

The terms "embryonic stem cell" and "ES cell" refer to cells derived from mammalian embryos or blastocysts, which are self-renewing and have the ability to yield many or all of the cell types present in a mature animal. Human embryonic stem cell lines suitable for use with the methods and compositions of the present invention include but are not limited to those produced by the following institutions: BresaGen, Inc., Athens, Ga.; CyThera, Inc., San Diego, Calif.; ES Cell International, Melbourne, Australia; Geron Corporation, Menlo Park, Calif.; Goteborg University, Goteborg, Sweden; Karolinska Institute, Stockholm, Sweden; Maria Biotech Co. Ltd.—Maria Infertility Hospital Medical Institute, Seoul, Korea; MizMedi Hospital—Seoul National University, Seoul, Korea; National Centre for Biological Sciences/Tata Institute of Fundamental Research, Bangalore, India; Pochon CHA University, Seoul, Korea; Reliance Life Sciences, Mumbai, India; Technion University, Haifa, Israel; University of California, San Francisco, Calif.; and Wisconsin Alumni Research Foundation, Madison, Wis. The human ES cells listed on the Human Embryonic Stem Cell Registry to be created by the National Institutes of Health find use in the methods and compositions of the present invention. However, human ES cells not listed on the NIH registry are also contemplated to find use in embodiments of the present invention (e.g., when it is desirable to prevent ES contamination with nonhuman-derived materials).

As used herein, the term "embryonic" means undeveloped or related to an embryo. In humans, the term embryo refers to the developing organism from about two weeks after fertilization to the end of seventh or eighth week. As used herein, the term "fetal" refers to in utero development occurring after the embryonic period. In humans, the term "fetus" refers to the developing organism after about seven or eight weeks of pregnancy. In some embodiments of the present invention, the feeder cells may be of fetal or embryonic origin.

As used herein, the terms "transplant cells" and "graft material" refer broadly to the component (e.g., tissue or cells) being grafted, implanted or transplanted.

A transplanted tissue may comprise a collection of cells of identical or similar composition, or derived from an organism (e.g., a donor), or from an in vitro culture (e.g., a tissue culture system). The term "suitable graft material" refers to tissue with the desired phenotype (e.g., renal cell morphology), which is free of deleterious contaminants (e.g., free of bacteria and fungi).

The term "recipient of transplanted cells" as used herein, refers broadly to the subject undergoing transplantation and receiving transplanted cells.

As used herein, the term "host" refers to any warm blooded mammal, including, but not limited to, humans, non-human primates, rodents, and the like, which is to be the recipient of a particular treatment. Typically, the terms "host" and "patient" are used interchangeably herein in reference to a human subject.

As used herein, the term "carrier" refers to a diluent, adjuvant, excipient, or vehicle with which a compound is administered. Such pharmaceutical carriers can be sterile liquids, such as water and oils, including those of petroleum, animal, vegetable, or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

As used herein, the term "therapeutically effective amount" refers to an amount sufficient to detectably reduce (e.g., by at least about 15 percent, preferably by at least 50 percent, more preferably by at least 90 percent, and most preferably prevent) a clinically significant deficit in the activity, function, and/or response of a host. Alternatively, a therapeutically effective amount is sufficient to cause an improvement in a clinically significant condition in a host.

As used herein, the term "heterologous gene" refers to a gene encoding a factor that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed). Heterologous genes may be introduced into stem or progenitor cells through molecular biology manipulation. The coding sequence of the heterologous gene is operatively linked to an expression control sequence. Generally a heterologous gene is first placed into a vector.

As used herein, the term "gene-modified stem cell" refers to a stem cell that has been transduced by a heterologous gene.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

GENERAL DESCRIPTION OF THE INVENTION

Embryonic Stem (ES) cells provide a potentially unlimited source for generating highly specialized cells and tissues in vitro. Such in vitro produced are excellent model systems for physiological studies and may ultimately have therapeutic applications. Indeed, ES cells can be directed to differentiate along specific cell lineage pathways such as pancreatic cells (see, e.g., Kania, G., et al., (2003) Methods Enzymol 365, 287-303; Lumelsky, N., et al., (2001) Science 292, 1389-94; each herein incorporated by reference in their entireties), motor neurons (see, e.g., Wichterle, H., et al., (2002) Cell 110, 385-97; herein incorporated by reference in its entirety), and hematopoietic cells (see, e.g., Daley, G. Q. (2003) Ann N Y Acad Sci 996, 122-31; herein incorporated by reference in its entirety). The ability to differentiate ES cells selectively depends in part on secreted growth and differentiation factors that mimic the environment of a particular cell lineage.

In birds and mammals, the mesoderm is compartmentalized along the medio-lateral axis into paraxial, intermediate, and the lateral plate mesoderm. Much of the urogenital system is derived from the intermediate mesoderm, which undergoes sequential patterning into pro-, meso-, and metanephric structures along the anterior-posterior axis (see, e.g., Dressler, G. R. (2002). Development of the Excretory System. In Mouse Development Patterning, Morphogenesis, and Organogenesis, (ed. J. Rossant and P. T. Tam), pp. 395-420. San Diego, Calif.: Academic Press; herein incorporated by reference in its entirety). The Pax2 and Pax8 genes are expressed early in the intermediate mesoderm and are required for formation of the first epithelial ducts (see, e.g., Bouchard, M., et al., (2002) Genes Dev 16, 2958-70; herein incorporated by reference in its entirety). In the chick embryo, activation of Pax2 expression requires signals from paraxial mesoderm, though these remain largely uncharacterized (see, e.g., Mauch, T. J., et al., (2000) Dev Biol 220, 62-75; herein incorporated by reference in its entirety). The adult kidney or metanephros is formed by reciprocal inductive interactions between the ureteric bud epithelium and the metanephric mesenchyme. This induced mesenchyme is thought to provide a pool of renal stem cells capable of generating much of the tubular and glomerular epithelia (see, e.g., Herzlinger, D., et al., (1992) Development 114, 565-72; herein incorporated by reference in its entirety). Among the early genes expressed in the metanephric mesenchyme are Pax2, Wt1, gdnf, six1 and six2 (see, e.g., Bouchard, M., et al., (2002) Genes Dev 16, 2958-70; Dressler, G. R. (2002). Development of the Excretory System. In Mouse Development: Patterning, Morphogenesis, and Organogenesis, (ed. J. Rossant and P. T. Tam), pp. 395-420. San Diego, Calif.: Academic Press; Yu, J., et al., (2004) Curr Opin Genet Dev 14, 550-7; each herein incorporated by reference in their entireties). Subsequent to induction, many additional secreted factors, including Wnts and BMPs, stimulate epithelia cell differentiation and refine the pattern of the developing nephron.

Certain differentiation factors have been identified and employed in renal cell cultures. TGF-β1 has been shown to transform a monolayer of renal proximal tubule cells in primary culture into a three-dimensional adhesive aggregate of cells (see, e.g., Humes et al, Lab. Invest. 64:538-545 (1991); herein incorporated by reference in its entirety). EGF has been shown to be a potent growth promoter for renal epithelial cells (see, e.g., Norman et al, Am. J. Physiol. 253:F299-F309 (1987); herein incorporated by reference in its entirety). Retinoic acid has been reported to increase laminin synthesis in embryonic cell lines by promoting laminin gene transcription (see, e.g., Dziadpk et al, Devel. Biol. 111:372-382 (1985); Vasios et al, Proc. Natl. Acad. Sci. (USA) 86:9099-9103 (1989); and Rogers et al, J. Cell. Biol. 110:1767-1777 (1990); each herein incorporated by reference in their entireties). However, the efforts of the prior art have all failed to evoke tubular epithelia in renal cell cultures.

In experiments conducted during the course of the present invention, markers and biochemical pathways for early kidney development were used to differentiate ES cells into renal epithelial progenitor cells. In preferred embodiments, retinoic acid and activin-a stimulated expression of early intermediate mesodermal markers, and addition of bmp-7 further enhanced the ability of these cells to contribute to developing tubules in a kidney organ culture system. As such, in preferred embodiments, the present invention provides a nephrogenic cocktail of factors that promotes differentiation into intermediate mesoderm-like cells and ultimately renal epithelial cells is provided. Such in vitro generated cells are useful for the development of bioartificial organs (see, e.g., Fissell, W. H. and Humes, H. D. (2003) Transplant Proc 35, 2837-42; herein incorporated by reference in its entirety) or cell based therapies in chronic or acute renal failure, as well as for research and drug screening applications.

DETAILED DESCRIPTION OF THE INVENTION

The present invention relates generally to the field of cell biology of embryonic cells and renal progenitor cells. In particular, the present invention relates to the directed differentiation of embryonic stem cells to form cells of renal lineage, using special culture conditions and selection techniques.

In some embodiments of the present invention, stem cells (e.g. embryonic stem cells) are cultured in the presence of a composition comprising two or more of a first agent capable of activating the retinoic acid signaling pathway, a second agent capable of activating the activin-a pathway, and a third agent capable of activating the bmp-7 pathway. The stem cells may further comprise one or more other heterologous genes of interest (e.g., a therapeutic gene or a reporter gene). In certain preferred embodiments, the stem cells further comprise a selectable marker or a detectable marker (e.g., to allow detection or isolation of transfected cells and/or to allow monitoring of cells in vivo).

The present invention further provides methods for the transplantation of expanded activin-a/retinoic acid/bmp-7-treated stem cells into host organisms. Cells may be transplanted for therapeutic applications (e.g., treatment of renal disease) and/or for expression of a transgene, or may be transplanted to monitor cell localization and maintenance in a host (e.g., over time or in response to further treatment with drugs).

Certain preferred embodiments of the present invention are described in detail below. The present invention is not limited to these particular described embodiments. The description is provided in the following section: I) Identification and in vitro Isolation of Stem Cells; II) Differentiation Factors; III) Heterologous Gene Expression; and IV) Transplantation.

I. Identification and in vitro Isolation of Stem Cells

Stem cells are undifferentiated cells that can give rise to a succession of mature functional cells. The present invention can be practiced using stem cells from a variety of vertebrate species. Included are stem cells from mice, humans, primates, domestic animals, livestock, and other non-human mammals.

In preferred embodiments, the present invention utilizes embryonic stem cells. Embryonic stem cells are pluripotent cells derived from the inner cell mass of pre-implantation embryos. (Evans et al., Nature, Vol. 292:154-156 (1981); herein incorporated by reference in its entirety). Embryonic stem cells can differentiate into any cell type in vivo (Bradley, et al., Nature, Vol. 309:255-256 (1984); Nagy, et al., Development, Vol. 110:815-821 (1990); each herein incorporated by reference in their entireties) and into a more limited variety of cells in vitro (Doetschman, et al., J. Embryol. Exp. Morph., Vol. 87:27-45 (1985); Wobus, et al., Biomed. Biochim. Acta, Vol. 47:965-973 (1988); Robbins, et al., J. Biol. Chem., Vol. 265:11905-11909 (1990); Schmitt, et al., Genes and Development, Vol. 5:728-740 (1991); each herein incorporated by reference in their entireties).

Embryonic stem cells, however, are more difficult to maintain in the laboratory and require the addition of a differentiation inhibitory factor (commonly referred to as leukemia inhibitory factor (or LIF) in the culture medium to prevent spontaneous differentiation (Williams, et al., Nature, Vol. 336:684-687 (1988); Smith, et al., Nature, Vol. 336:688-690 (1988); Gearing, et al., Biotechnology, Vol. 7:1157-1161 (1989); Pease, et al., Dev. Biol., Vol. 141:344-352 (1990); each herein incorporated by reference in their entireties). LIF is a secreted protein and can be provided by maintaining embryonic stem cells on a feeder layer of cells that produce LIF (Evans et al., Nature, Vol. 292:154-156 (1981); Robertson, Teratocarcinomas and Embryonic Stem Cells: A Practical Approach, Washington, D.C.: IRL Press (1987); herein incorporated by reference in its entirety) or by the addition of purified LIF (Williams, et al., 1988; Smith, et al., 1988; Gearing, et al., 1989; Pease, et al., Exp. Cell Res., Vol. 190:209-211 (1990); each herein incorporated by reference in their entireties) to the medium in the absence of feeder layers.

Differentiation of embryonic stem cells into a heterogeneous mixture of cells occurs spontaneously if LIF is removed, and can be induced further by manipulation of culture conditions (Doetschman, et al., J. Embryol. Exp. Morph., Vol. 87:27-45 (1985); Wobus, et al., Biomed. Biochim. Acta, Vol. 47:965-973 (1988); Robbins, et al., J. Biol. Chem., Vol. 265:11905-11909 (1990); Schmitt, et al., Genes and Development, Vol. 5:728-740 (1991); Wiles, et al., Development, Vol. 111:254-267 (1991); Gutierrez-Ramos, et al., Proc. Nat. Acad. Sci., Vol. 89:9111-9175 (1992); each herein incorporated by reference in their entireties). Embryonic stem cell differentiation can be variable between different established embryonic stem cell lines and even between laboratories using the same embryonic stem cell lines.

Embryonic stem cells can be isolated, for example, from blastocysts of members of the primate species (see, e.g., Thomson et al., Proc. Natl. Acad. Sci. USA 92:7844, 1995; herein incorporated by reference in its entirety). Human embryonic stem (hES) cells can be prepared from human blastocyst cells using the techniques described by Thomson et al. (see, e.g., U.S. Pat. No. 5,843,780; Science 282:1145, 1998; Curr. Top. Dev. Biol. 38:133 ff., 1998; each herein incorporated by reference in their entireties) and Reubinoff et al, Nature Biotech. 18:399, 2000, which also is herein incorporated by reference in its entirety.

The methods of the present invention are not limited to the use of primate embryonic stem cells. Indeed, the use of embryonic stem cells from other species are contemplated, including, but not limited to mice, rats, pigs, cattle and sheep. Methods for obtaining pluripotent cells from these species have been previously described. See, e.g., U.S. Pat. Nos. 5,453,357; 5,523,226; 5,589,376; 5,340,740; and 5,166,065 (all of which are specifically incorporated herein by reference); as well as, Evans, et al., Theriogenology 33(1):125-128, 1990; Evans, et al., Theriogenology 33(1):125-128, 1990; Notarianni, et al., J. Reprod. Fertil. 41(Suppl.):51-56, 1990; Giles, et al., Mol. Reprod. Dev. 36:130-138, 1993; Graves, et al., Mol. Reprod. Dev. 36:424-433, 1993; Sukoyan, et al., Mol. Reprod. Dev. 33:418-431, 1992; Sukoyan, et al., Mol. Reprod. Dev. 36:148-158, 1993; Iannaccone, et al., Dev. Biol. 163:288-292, 1994; Evans & Kaufman, Nature 292: 154-156, 1981; Martin, Proc Natl Acad Sci USA 78:7634-7638, 1981; Doetschman et al. Dev Biol 127:224-227, 1988); Giles et al. Mol Reprod Dev 36:130-138, 1993; Graves & Moreadith, Mol Reprod Dev 36:424-433, 1993 and Bradley, et al., Nature 309:255-256, 1984.

The present invention also contemplates the use of non-embryonic stem cells. Mesenchymal stem cells (MSCs) can be derived from marrow, periosteum, dermis and other tissues of mesodermal origin (See, e.g., U.S. Pat. Nos. 5,591,625 and 5,486,359, each of which is incorporated herein by reference). MSCs are the formative pluripotential blast cells that differentiate into the specific types of connective tissues (i.e. the tissues of the body that support the specialized elements; particularly adipose, areolar, osseous, cartilaginous, elastic, marrow stroma, muscle, and fibrous connective tissues) depending upon various in vivo or in vitro environmental influences. Although these cells are normally present at very low frequencies in bone marrow, various methods have been described for isolating, purifying, and greatly replicating the marrow-derived mesenchymal stems cells in culture, i.e. in vitro (See also U.S. Pat. Nos. 5,197,985 and 5,226,914 and PCT Publication No. WO 92/22584, each of which are incorporated herein by reference).

II. Differentiation Factors

Renal progenitor cells of the present invention are obtained by culturing, differentiating, or reprogramming stem cells in a special growth environment that enriches for cells with a desired phenotype (e.g., renal progenitor cells). These methods are applicable to many types of stem cells, including, for example, murine or primate pluripotent stem cells.

Stem cell differentiation takes place in a culture environment comprising a suitable substrate and a nutrient medium to which the differentiation agents are added. Suitable substrates include solid surfaces coated with a positive charge, such as a basic amino acid, exemplified by poly-L-lysine and polyornithine. Substrates can be coated with extracellular matrix components. Other permissive extracellular matrixes include Matrigel (extracellular matrix from Engelbreth-Holm-Swarm tumor cells) and laminin. Also suitable are combination substrates, such as poly-L-lysine combined with fibronectin, laminin, or both.

The present invention is not limited to particular differentiation agents. In preferred embodiments, the present invention provides activin-a (see, e.g., Hollnagel, A., et al., J. (1999) J. Biol. Chem. 274:19838-19345; herein incorporated by reference in its entirety), bmp-4 (see, e.g., Hollnagel, A., et al., J. (1999) J. Biol. Chem. 274:19838-19345; Wiles, M. V., et al., (1999) Exp. Cell. Res. 247:241-248; each herein incorporated by reference in its entirety), bmp-7 (see, e.g., M. Komaki, et al., (2004) J. Cell. Sci. 117(8):1457-1468; herein incorporated by reference in its entirety) and retinoic acid (see, e.g., Slager, H. G., et al., (1993) Dev. Genet. 14:212-224; Bain, G., et al., (1995) Dev. Biol. 168:342-357; each herein incorporated by reference in its entirety). Additional suitable differentiation agents include, but are not limited to, epidermal growth factor (EGF), transforming growth factor α (TGF α), any type of fibroblast growth factor (exemplified by FGF-4, FGF-8, and basic fibroblast growth factor=bFGF), platelet-derived growth factor (PDGF), insulin-like growth factor (IGF-1 and others), high concentrations of insulin, sonic hedgehog, members of the neurotrophin family (such as nerve growth factor, neurotrophin 3, brain-derived neurotrophic factor), additional bone morphogenic proteins, and ligands to receptors that complex with gp 130 (such as LIF, CNTF, and IL-6). Also suitable are alternative ligands and antibodies that bind to the respective cell-surface receptors for the aforementioned factors. Typically, a cocktail containing a plurality of differentiation agents is used, which may comprise 2, 3, 4, or more of the agents listed above or in the examples below. The present invention may also be practiced with differentiation factor variants, such as deletion mutants, sequence change variants, truncated versions of particular differentiation factor, small molecule mimetics, etc.

In preferred embodiments, the present invention provides renal cells with tubular epithelia generated through differentiation of stem cells with a nephrogenic cocktail (e.g., activin-a, bmp-7, and retinoic acid, or variants thereof).

III. Modulating Downstream Differentiation Factor Pathway Molecules

In some embodiments, stem cells are expanded with a molecule that activates a downstream differentiation factor pathway molecule (e.g., pathway related to retinoic acid, activin-a, bmp-4, and/or bmp-7), or derivatives of any of these compounds or similar compounds). In other embodiments, the function of stem cells are modulated with a molecule that inhibits a downstream growth factor pathway molecule, such as a molecule that inhibits a pathway related to retinoic acid, activin-a, bmp-4, and/or bmp-7.

IV. Heterologous Gene Expression

Certain embodiments of the present invention employ heterologous genes in the stem cells. In some embodiments, the heterologous gene is a gene of interest such as a therapeutic gene or a reporter gene.

Vectors for ex vivo administration of a gene encoding a heterologous gene may be introduced via any strategy. Vectors can be introduced to transduce the desired host cells ex vivo by methods including, but not limited to, β-catenin (see U.S. Pat. No. 6,465,249, herein incorporated by reference), transfection, electroporation, microinjection, cell fusion, DEAE dextran, calcium phosphate precipitation, lipofection, use of a gene gun, viral vector, DNA vector transporter, and the like. Any gene of interest may be expressed in the stem cells. Examples of genes that find use with the present invention include, but are not limited to, therapeutics genes, reporter genes, and selectable markers. Reporter genes may be expressed, for example, to monitor the expansion, differentiations, and maintenance of cells in vivo. Selectable markers may be used, for example, to select cells that have undergone a successful transfection event.

V. Transplantation

The present invention provides cells and methods for transplantation into host organisms. Transplantation of stem cells treated and expanded through exposure to differentiation factors (e.g., activin-a, retinoic acid, bmp-7) into a host may be used, for example, to provide a source of stem cells for generating and supplying differentiated products, to express a gene of interest, and to detect and characterize cell expansion and differentiation in vivo (e.g., to provide detectable cells for testing drugs that influence cell expansion, differentiation, and cell fate in vivo). As such, both human and non-human animal hosts find use in the present invention.

In preferred embodiments, where cells are to be used for therapeutic purposes, the stem cell is preferably obtained from the subject in need of treatment, and then after expansion, the resulting stem cell expanded through exposure to differentiation factors (e.g., activin-a, retinoic acid, bmp-7) is placed back into the host (See, WO 99/61589 for methods of reintroduction into hosts, herein incorporated by reference in its entirety).

EXPERIMENTAL

The following example serves to illustrate certain preferred embodiments and aspects of the present invention and is not to be construed as limiting the scope thereof.

Example 1

This example describes cell culture and microinjection techniques utilized in experiments conducted during the course of the present invention. Mouse ES cells (R26) were grown in high glucose DMEM (GIBCO BRL), 10% fetal bovine serum (Atlanta Biologicals), 0.1 mM β-mercaptoethanol (Sigma), 4 mM glutamine (GIBCO BRL), 20 unit/ml PEN/STREP (GIBCO BRL), 0.1 mg/ml G418 (GIBCO BRL), and $10^3$ unit/ml rLIF (Chemicon) on a 0.1% gelatin-coated tissue culture plate at 37° C. $CO_2$ incubator for 2 days. The ES cells were transferred using 0.05% trypsin plus 0.53 mM EDTA (GIBCO BRL) to a 100-mm bacteriological petri dish (Falcon) to induce embryoid body (EB) formation. The EB suspension was cultured in the same medium without rLIF for 2 days and then transferred to 60-mm tissue culture plates coated with 0.1% gelatin. Each 60-mm tissue culture plate contained about 100 EBs. The EBs were grown without growth factors or in the presence of the following growth factors: 0.1 μM retinoic acid (RA), 10 ng/ml activin-a, 50 ng/ml bmp4, or 50 ng/ml bmp-7 (R & D Systems). The cells were trypsinized and resuspended with 10 μl phosphate buffered saline to make final concentration of $10^8$ cells/ml, and microinjected with a very fine needle into E11.5 or E12.5 embryonic kidneys on a transwell plate in which 0.9 ml DMEM was added. The kidneys were cultured at 37° C. $CO_2$ incubator for 3-5 days. For in vitro induction experiments, embryoid bodies were cultured on methyl-cellulose plates for 5 days with or without nephrogenic factors and then placed next to a piece of E12.5 spinal cord on a transwell filter.

Example II

This example describes a reverse transcription—PCR(RT-PCR) analysis technique utilized in experiments conducted during the course of the present invention. Total RNA was extracted by using TRIZOL reagent (GIBCO BRL). One unit of DNase I (Boehringer Mannheim) was added to 1 μg RNA and the mixture was incubated at 37° C. for 30 min. The isolated RNA by phenol/chloroform method was used for RT-PCR template. Superscript™ One-Step RT-PCR with Platinum Taq (Invitrogen) was utilized for cDNA synthesis and PCR amplification in a Peltier Thermal Cycler (MJ Research). The primer pairs for RT-PCR were as follows:

```
Pax-2:
                                       (SEQ ID NO: 1)
CAGCCTTTCCACCCAACG, GTGGCGGTCATAGGCAGC

Lim-1:
                                       (SEQ ID NO: 2)
CAAAGAGAACAGCCTCCACTCG, GGATGTGCCAGGATGTCAGTAAATC gdnf:
                                       (SEQ ID NO: 3)
AAGGTCACCAGATAAACAAGCGG, CATAGCCCAAACCCAAGTCAGTG Eya1:
                                       (SEQ ID NO: 4)
CTAACCAGCCCGCATAGCCG, TAGTTTGTGAGGAAGGGGTAGG Six2:
                                       (SEQ ID NO: 5)
GCACCTCCACAAGAATGAAAGC, TGAGCAACAGAGCGGGACTG wnt4:
                                       (SEQ ID NO: 8)
AACTGGAGAAGTGTGGCTGTGACCG, (SEQ ID NO: 7)
CATCTGTATGTGGCTTGAACTGTGC
```

```
                                -continued
Wt1:
                                                (SEQ ID NO: 9)
CACCAAAGGAGACACACAGGT, (SEQ ID NO: 10)
CACACTTTCCTGCCTGGGAT cadherin-6:
                                                (SEQ ID NO: 11)
TTTGTGGTCCAAGTCACGGC, (SEQ ID NO: 12)
CATCGGCATCACTGGCTTTG oct-4:
                                                (SEQ ID NO: 13)
AGCTGCTGAAGCAGAAGAGG, (SEQ ID NO: 14)
GGTTCTCATTGTTGTCGGCT GAPDH:
                                                (SEQ ID NO: 15)
TCCGCCCCTTCTGCCGATG, (SEQ ID NO: 16)
CACGGAAGGCCATGCCAGTGA
```

All pairs were written 5' to 3' with the top and bottom strands in order. The cycling conditions were as follows: c-DNA synthesis (1 cycle of 50° C. for 30 min), pre-denaturation (94° C. for 2 min), and PCR amplification (30 cycles of 94° C. for 1 min, 58° C. for 2 min, and 72° C. for 2 min). The thermal cycler was programmed such that cDNA synthesis was followed automatically with PCR amplification. Each PCR reaction included a no-template control in which water was added instead of the RNA. The different amount of RNA (1 ng, 10 ng, 100 ng, and 1 µg) was used to assure linearity and The RT-PCR products were synthesized using 100 ng RNA for GDNF, Pax-2, Lim-1, Six-2, and Eya-1, 10 ng RNA for WT-1, Wnt-4, Oct-4 and GAPDH. A single step RT-PCR was sufficient to detect all mRNAs list above.

Example III

This example describes immunohistochemistry techniques utilized in experiments conducted during the course of the present invention. Embryoid bodies were fresh frozen in OCT and sectioned at 10 microns in a cryostat. After air drying, sections were fixed in 3% PFA for 10 min and washed in PBS, 0.1% Tween 20 (PBST). Antibodies were incubated for 2 h at room temperature in PBST, 2% goat serum. Primary antibodies used were: rabbit anti-Pax2 (Covance Inc.), mouse anti-pan-cytokeratin (Sigma), mouse anti-E-cadherin (Cell Signaling Technology), mouse anti-b-catenin (Cell Signaling Technology), rabbit anti-laminin (Sigma), and FITC-lotus tetragonobulus agglutinin (LTA, Sigma). After washing two times in PBST, fluorescent conjugated secondary antibodies were used. Images were captured on a Nikon ES800 fluorescent scope with a SPOT digital camera.

Example IV

This example describes lacZ staining techniques utilized in experiments conducted during the course of the present invention. For whole mounts, kidney rudiments were fixed in 0.2% gluteraldehyde, 1% formaldehyde, 0.02% NP-40 in PBS for 10 min. at room temperature (RT), washed in PBS and stained overnight at RT in PBS with 5 mM $K_3Fe(CN)_6$, 5 mM $K_4Fe(CN)_6$, 2 mM MgCl2, 1 mg/ml X-Gal. After washing in PBS, whole rudiments were incubated with anti-laminin (Sigma, 1:100) in PBS, 0.1% Tween-20, 2% goat serum or FITC conjugated lectin tetragonobulus (Sigma, 1:50). Detection of anti-laminin was with TRITC conjugated anti-rabbit secondary antibodies. Washes were done at RT 3-4 times in PBS, 0.1% Tween-20. For staining of sections, fresh frozen kidney rudiments were cut at 25 microns and fixed. Staining was done at 32° C. overnight in X-gal buffer and sections washed in PBST. Anti-laminin and FITC conjugated LTA was used to visualize tubules.

Example V

To examine the ability of ES cells to differentiate into intermediate mesoderm under controlled conditions, embryoid bodies (EBs) were formed in culture over a 5 day period. The Rosa26 ES cell line was used as it is tagged with a ubiquitously expressed lacZ gene. Subsequently, the EBs were cultured with increasing concentrations of retinoic acid, activin-a, or both and grown for an additional 5-7 days. The concentrations of retinoic acid and activin-a ranged in ten fold increments from $10^{-6}$ to $10^{-12}$ M and 1 ng/ml to 100 ng/ml respectively. These two factors were chosen initially because in combination they are able to expand the pronephric field in the *Xenopus* embryo (see, e.g., Ariizumi, T. and Asashima, M. (2001) Int J Dev Biol 45, 273-9; herein incorporated by reference in its entirety). Experiments utilized retinoic acid and activin-a singly and in combination over all concentrations. Subsequently, bmp4 and bmp-7 were added as both are expressed in the mesonephric and metanephric regions.

To assess the efficacy of growth and differentiation factors, RNA was isolated from embryoid bodies and tested by RT-PCR for the expression of early nephrogenic markers (see, e.g., Davies, J. A. and Fisher, C. E. (2002) Exp Nephrol 10, 102-13; Dressler, G. R. (2002). Development of the Excretory System. In Mouse Development: Patterning, Morphogenesis, and Organogenesis, (ed. J. Rossant and P. T. Tam), pp. 395-420. San Diego, Calif.: Academic Press; each herein incorporated by reference in their entireties). The Pax2 and lim1 genes are among the earliest markers of the intermediate mesoderm, from which the renal epithelial cells arise. Subsequently, Pax2 is expressed in all epithelial precursors of the kidney. The Wt1 gene is expressed at low levels in renal mesenchyme and epithelial cells and at high levels in the podocytes. The Eya1, Six2 and gdnf genes are expressed in early kidney mesenchyme but not their epithelial derivatives. Wnt4 is highly expressed in early mesenchymal aggregates and their epithelial derivatives, whereas cadherin-6 is an early marker for proximal tubules precursors. Oct4 expression is a marker of pluripotency in ES cells and is not found in more differentiated lineages (see, e.g., Fuhrmann, G., et al., (2001) Dev Cell 1, 377-87; herein incorporated by reference in its entirety).

As shown in FIG. 1, a significant shift in the pattern of gene expression was evident upon addition of retinoic acid and differentiation promoting factors. In the absence of LIF, the EBs express a large set of markers that reflect, in part, the heterogeneity of the EBs. Some of the markers were positive in EBs in the absence of factors. However, the combination of retinoic acid and activin-a (RA) was highly effective in stimulating Pax2 induction. Consistent with the loss of pluripotency, the expression of Oct4 was suppressed in EBs and in all treated cultures. The expression of six2 and Eya1 was not upregulated with the addition of factors, though both genes are known to be expressed in the metanephric mesenchyme but not in epithelial cells. Pax2, gdnf and Wt1 were only expressed in the treated EBs. Further addition of bmp4 (RA4) suppressed expression of early intermediate mesoderm specific markers, such as lim1, Pax2, and Wt1. However, bmp-7 treated EBs (RA7) showed only a slight reduction in Pax2 levels but increased cadherin-6 levels, a gene expressed in induced metanephric mesenchyme as cells convert to a polarized epithelia.

Example VI

Figure 2:
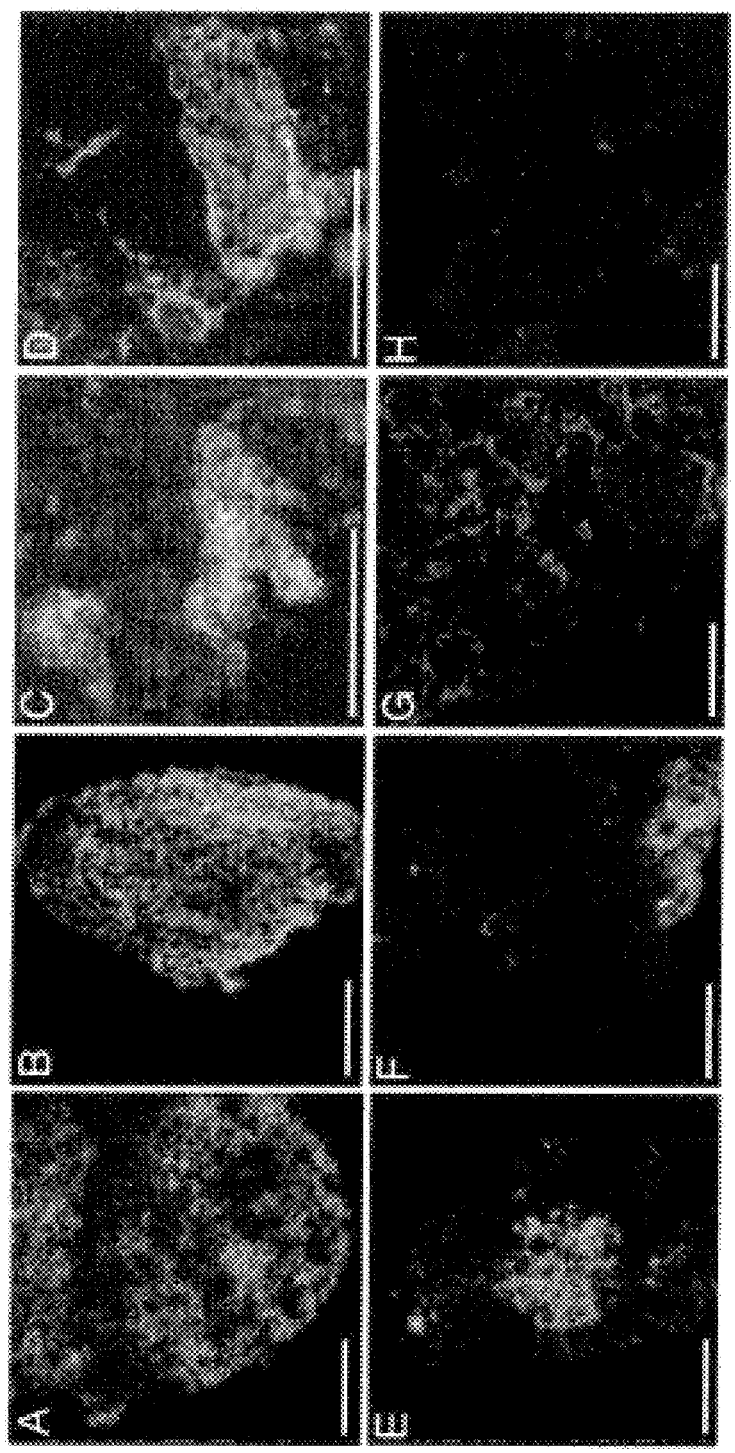
FIG. 2 shows immunostaining of embryoid bodies. Embryoid bodies were cultured for 5 days in methylcellulose treated dishes with and without nephrogenic factors (RA7) and sectioned. A) RA7 treated EB stained for Pax2 (red) and b-catenin (green). B) Control EB cultured without factors stained for Pax2 (red) and b-catenin (green). C) RA7 treated EB stained for Pax2 (red) and E-cadherin (green). D) Neighboring section to C stained for laminin (red) and cytokeratin (green). E) RA7 treated EB stained for cadherin-6 (red) and cytokeratin (green). F) Control EB stained for cadherin-6 (red) and cytokeratin (green). G) RA7 treated EB stained for laminin (red). H) Control EB stained for laminin (red). Magnification bars are 100 microns.

The induction of Pax2, Wt1, lim1, gdnf and cadherin-6 that cells within the EBs expressed markers appropriate for intermediate mesoderm and early derivatives of the metanephric mesenchyme. To gauge the proportion of cells within the EBs expressing these markers, immunohistochemistry was utilized on sections through treated and control EBs (see FIG. 2). Widespread nuclear Pax2 staining was evident in EBs cultured in the nephrogenic cocktail (bmp-7, activin-a, and retinoic acid), but not in control EBs (FIGS. 2 A, B). Large patches of E-cadherin positive cells were also observed, exhibiting characteristic cell surface staining. The E-cadherin positive regions covered more area in the EBs cultured with nephrogenic factors. Similarly, cytokeratins were observed in control EBs but more positive areas were seen in treated EBs. In treated cultures, some Pax2 positive cell clusters also expressed E-cadherin, epithelial cytokeratins and were surrounded by a laminin containing basement membrane (FIG. 2 C, D). In treated cultures, cytokeratin expressing cells were frequently adjacent to cells expressing cadherin-6, but these markers were rarely expressed in the same cells (FIG. 2 E, F). In control EBs, few cells exhibited the characteristic cell surface expression of cadherin-6. Strong laminin staining was found throughout the treated EBs (FIG. 2 G, H). In control EBs, laminin staining was not very prominent.

Example VII

Figure 3:
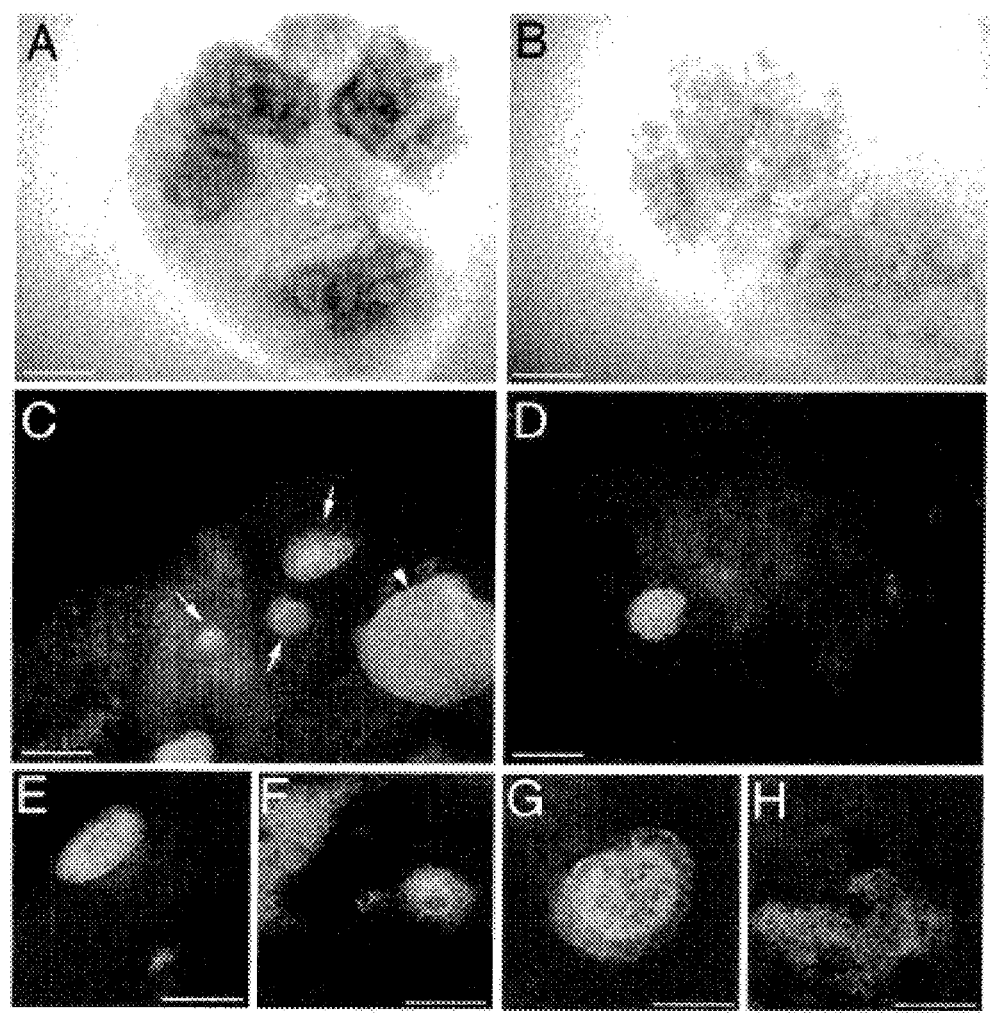
FIG. 3 shows co-culture of embryoid bodies with spinal cord. Embryoid bodies were cultured for 5 days with or without nephrongeic factors, placed next to embryonic spinal cord on a transwell filter and cultured for an additional 4 days. A) Phase contrast of RA7 treated EBs surrounding a piece of E12.5 spinal cord (sc). B) Phase contrast of control EBs surrounding a piece of E12.5 spinal cord. C-H) Whole mount antibody staining for Pax2 (red), E-cadherin (green), and laminin (blue) of EBs after co-culture with spinal cord. C) RA7 treated EBs exhibit Pax2 positive tubules (arrows) that also express E-cadherin and are surrounded by laminin containing basement membrane. Some large E-cadherin positive aggregates are also present that do not express Pax2 (arrowhead). D) Control EB stained exhibits no Pax2 positive tubules, diffuse laminin staining and the occasional E-cadherin positive aggregate. E, F, G) Examples of tubules found in RA7 treated EBs after co-culture with spinal cord. H) Typical control EB after co-culture with spinal cord. Magnification bars are 500 microns for A & B and 100 microns for C-H.

The metanephric mesenchyme expresses both Pax2 and Wt1 prior to induction by the ureteric bud and epithelial cell polarization. Induction can be mimicked in vitro by co-culturing metanephric mesenchyme with embryonic spinal, a strong heterologous inducer. Thus, embryoid bodies cultured in nephrogenic factors were placed next to isolated embryonic spinal cord on transwell filters (FIG. 3). After 4 days in culture, spinal cord induced multiple epithelial cysts and tubule like structures in EBs treated with nephrogenic factors (FIG. 3 A, C, E-G). Many of these epithelial structures expressed Pax2 and all expressed E-cadherin. Pax2 positive epithelial structures were frequently surrounded by a laminin containing basement membranes. EBs cultured in control media alone did not respond well to inductive signals. Some E-cadherin positive regions were observed, but these remained flattened and did not resemble epithelial cysts or tubules (FIG. 3 D, H).

Example VIII

Figure 4:
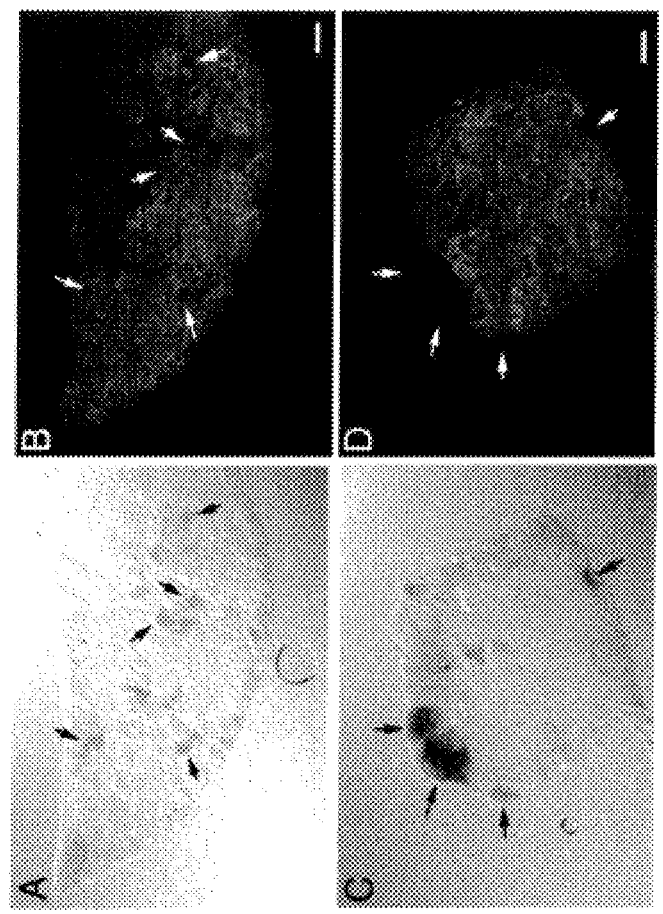
FIG. 4 shows injection of EB derived cells into E12.5 cultured kidneys. Cryosections from kidney rudiments were stained for lacZ expression (A & C) and with anti-laminin antibodies (B & D). A & B) LacZ positive cells from RA7 treated EBs were found predominantly tubular structures (arrows). C & D) Many lacZ positive cells from control EBs were found in large and small aggregates (arrows) that remained mesenchymal in appearance and were not surrounded by laminin containing basement membranes. Some blue cells from control EBs were also found in tubules. Magnification bars are 100 microns.

EBs were isolated after 5-7 days of culture, using the cocktail of nephrogenic factors (bmp-7, activin-a, and retinoic acid), and microinjected approximately 10-20 nl of the cell suspension (1,000-2,000 cells) into cultured kidney rudiments which had been dissected from E12.5 day embryos and placed on transwell filters. After the kidney rudiments were cultured for an additional 4-5 days, lacZ staining on whole mounts and cryosections and fluorescent antibody staining were performed with the kidney rudiments (FIG. 4). Kidneys injected with cells isolated from treated EBs exhibited lacZ staining in tubules throughout the organ culture (FIG. 4 A, B). The lacZ positive cells were mainly found in tubular structures, as determined by staining with anti-laminin. In contrast, cells isolated from EBs without any further treatment exhibited few lacZ positive tubules but large patches of lacZ positive cells along the peripheral mesenchyme and within the interstitum (FIG. 4 C, D). The cells were not found in tubular structures and more closely resembled undifferentiated mesenchyme, much like small embryoid bodies. In the absence of bmp-7, the proportion of lacZ positive tubules was reduced whereas addition of 100 ng/ml bmp4 completely inhibited the ability of EB cells to contribute to tubules in vitro. More than four independent experiments were performed with at least 8 kidneys injected per cell sample.

Example IX

Figure 5:
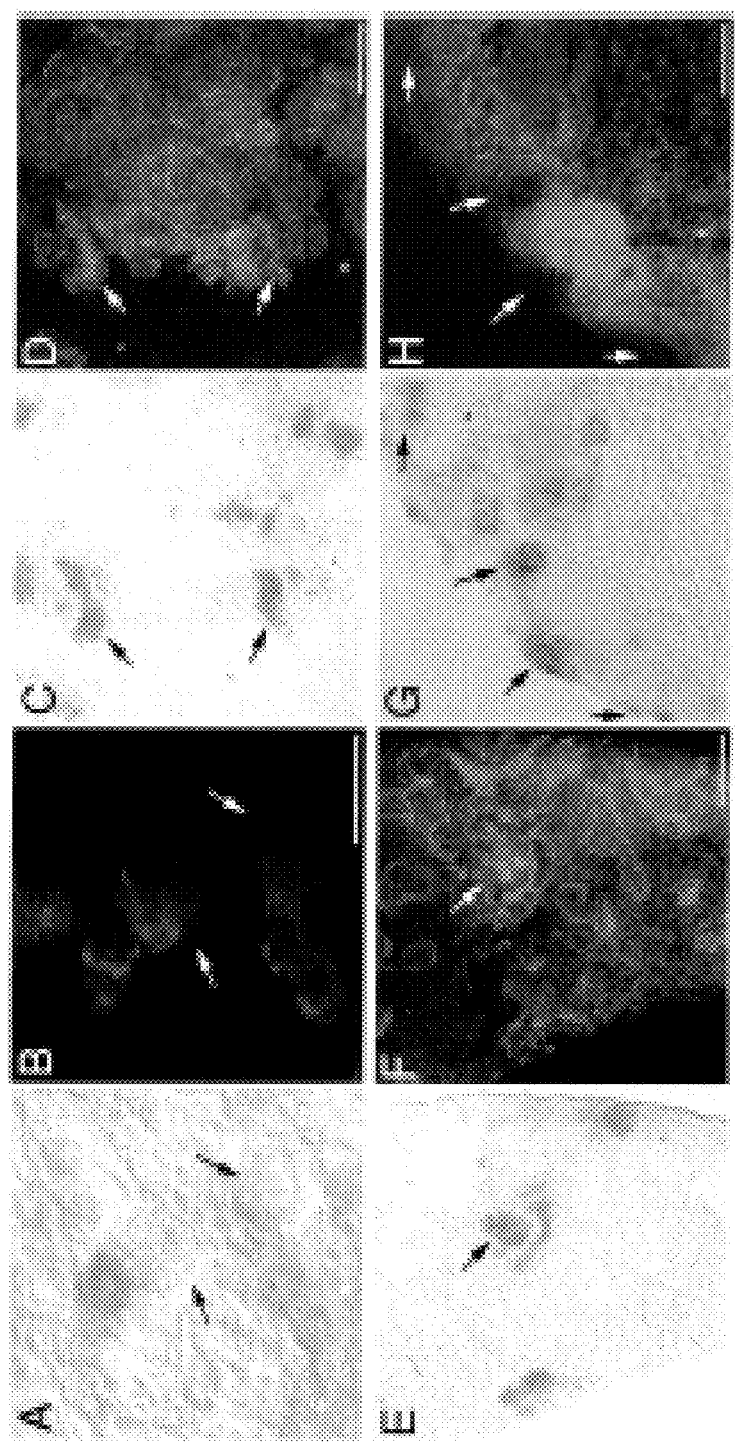
FIG. 5 shows characterization of EB derived tubule cells. E12.5 kidney rudiments were injected with RA7 treated EB cells (A-F) or control EB cells (G & H) and stained for lacZ, laminin, and LTA binding. A) Whole mount lacZ staining of tubule shows lacZ positive cells at the developing glomerular/proximal tubule junction. Arrows point to glomerular tufts. B) Laminin staining of same tissue as in A. C & D) Co-localization of lacZ positive cells in developing proximal tubules (arrows) that also stain with LTA lectin (green) and are surrounded by laminin containing basement membranes (red). E & F) Another developing proximal tubule derived from RA7 treated EB cells (arrow) stained as above. G & H) Many control EB cells localize to interstitial and peripheral mesenchyme (arrows), though a small number of lacZ positive cells are also found in tubules.

To better characterize the nature of the lacZ positive tubules derived from treated EB cells, whole mounts and sections from kidney rudiments 4 or 5 days after injection were utilized (FIG. 5). LacZ positive cells were found in tubules that connected to developing Bowman's capsules, but were never found in glomerular structures (FIG. 5 A, B). That many lacZ positive tubules were developing proximal tubules was confirmed by co-staining with anti-laminin and LTA (FIG. 5 C-F). FITC-LTA stains the lumens of proximal tubules during development (see, e.g., Cho, E. A., et al., (1998) Development 125, 4806-4815; herein incorporated by reference in its entirety) and co-localized with some, but not all LacZ positive cells in treated cultures. Untreated control EB cells rarely co-localized with LTA positive tubules as most LacZ positive clusters were mesenchymal in appearance (FIG. 5 G, H). As such, EB cells treated with the RA7 nephrogenic cocktail were able to contribute to developing tubules with increased frequency, compared to untreated EB cells. While bmp-7 enhanced the contribution to tubules, bmp4 treated EB cells did not integrate into developing tubules consistent with the inhibition of metanephric specific gene expression observed by RT-PCR.

Example X

Cell fusion was investigated with a genetic approach. The reporter ES cell line, R26R-EYFP (see, e.g., Srinivas, S., et al., (2001) BMC Dev Biol 1, 4; herein incorporated by reference in its entirety), contains a targeted insertion of enhanced yellow fluorescent protein (EYFP) into the ROSA26 locus, preceded by a loxP-flanked stop sequence. ES cells were treated with the nephrogenic cocktail (e.g., activin-a, retinoic acid, and bmp-7) and microinjected into kidney rudiments isolated from Ksp-Cre transgenic mice (see, e.g., Shao, X., et al., (2002) J Am Soc Nephrol 13, 1837-46; herein incorporated by reference in its entirety), which express Cre recombinase in the kidney epithelia. Cell fusion of R26R-EYFP with Cre expressing host cells would activate the fluorescent marker. However, no EYFP expressing cells in live or fixed cultures was detected implying no cell fusion with host tubules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A method for differentiating embryonic stem cells into renal proximal tubule cells comprising:
   a) providing:
      i) embryonic stem cells, wherein said embryonic stem cells are selected from the group consisting of murine embryonic stem cells and human embryonic stem cells; and
      ii) a composition comprising a first agent, a second agent, and a third agent;
   wherein said first agent is retinoic acid, wherein said second agent is activin-a, wherein said third agent is bmp-7;
   b) culturing said embryonic stem cells with said composition; and
   c) transplanting said cultured embryonic stem cells into kidney rudiments such that said cultured embryonic stem cells differentiate into renal proximal tubule cells.

2. The method of claim 1, wherein said kidney rudiments and said embryonic stem cells are from the same host.

* * * * *

SEQUENCE LISTING

<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
cagcctttcc acccaacg                                                      18

<210> SEQ ID NO 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
gtggcggtca taggcagc                                                      18

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
caaagagaac agcctccact cg                                                 22

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
ggatgtgcca ggatgtcagt aaatc                                              25

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
aaggtcacca gataaacaag cgg                                                23

<210> SEQ ID NO 6

<400> SEQUENCE: 6

000

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7

```
ctaaccagcc cgcatagccg                                                  20

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
tagtttgtga ggaagggta gg                                                22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
gcacctccac aagaatgaaa gc                                               22

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tgagcaacag agcgggactg                                                  20

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
aactggagaa gtgtggctgt gaccg                                            25

<210> SEQ ID NO 12
<211> LENGTH: 25
<212> TYPE: DNA
<213> ORGANISM: Artificial Sequence
<220> FEATURE:
<223> OTHER INFORMATION: Synthetic

<400> SEQUENCE: 12
catctgtatg tggcttgaac tgtgc                                            25

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
caccaaagga gacacacagg t                                                21

<210> SEQ ID NO 14
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 14
cacactttcc tgcctgggat                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tttgtggtcc aagtcacggc                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
catcggcatc actggctttg                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
agctgctgaa gcagaagagg                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ggttctcatt gttgtcggct                                              20

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
tccgcccctt ctgccgatg                                               19

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
cacggaaggc catgccagtg a                                            21
```